United States Patent [19]

Faustini et al.

[11] Patent Number: 4,757,061

[45] Date of Patent: Jul. 12, 1988

[54] 4-AMINO ANDROSTENDIONE DERIVATIVES AND PROCESS FOR THEIR PREPARATION

[75] Inventors: Franco Faustini, Milan; Roberto D'Alessio, Cinisello Balsamo; Vittoria Villa, Milan; Enrico di Salle, Milan; Paolo Lombardi, Milan, all of Italy

[73] Assignee: Farmitalia Carlo Erba, S.p.A., Milan, Italy

[21] Appl. No.: 828,637

[22] Filed: Feb. 10, 1986

[30] Foreign Application Priority Data

Feb. 15, 1985 [GB] United Kingdom ................. 8503940

[51] Int. Cl.[4] .......................... A61K 31/56; C07J 1/00

[52] U.S. Cl. .................................. 514/177; 260/397.3

[58] Field of Search ...................... 514/177; 260/397.3

[56] References Cited

FOREIGN PATENT DOCUMENTS 2002881 2/1969 France .
1042291 11/1961 United Kingdom .
1263992 2/1972 United Kingdom .
2048888A 12/1980 United Kingdom .

OTHER PUBLICATIONS

Chemical Abstracts; vol. 78 (1973) #97877n; Herzog et al.

Chemical Abstracts; vol. 82 (1975) #73298f; Smith et al. J. C. S. Chem. Comm. 1973, p. 72.

*Primary Examiner*—Leonard Schenkman
*Assistant Examiner*—Joseph A. Lipovsky
*Attorney, Agent, or Firm*—Murray and Whisenhunt

[57] ABSTRACT

The invention discloses 4-substituted androstendione derivatives of the following formula (I)

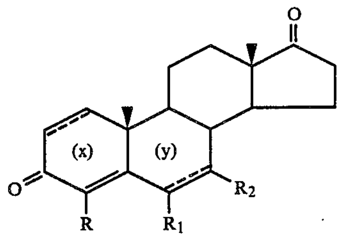

(I)

wherein

R is amino or substituted amino or azido, one of $R_1$ and $R_2$ is hydrogen and the other is hydrogen, alkyl, alkenyl or alkynyl, and (x) and (y) are each, independently, a single bond or a double bond.

The compounds of formula (I) are useful aromatase inhibitors.

6 Claims, No Drawings

4-AMINO ANDROSTENDIONE DERIVATIVES AND PROCESS FOR THEIR PREPARATION

The present invention relates to new 4-substituted androstendione derivatives, to a process for their preparation and to pharmaceutical compositions containing them. The invention provides compounds of the following formula (I)

(I)

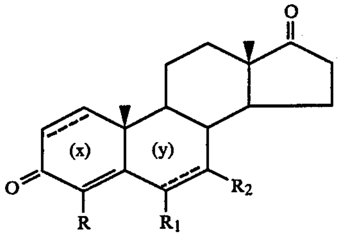

wherein
R is
(1) a group

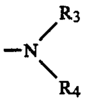

wherein each of $R_3$ and $R_4$ is, independently, hydrogen or unsubstituted $C_1$–$C_{22}$ alkyl;
(2) a group —$NHCOR_5$ wherein $R_5$ is
(a) hydrogen;
(b) $C_1$–$C_3$ alkoxy, benzyloxy or carboxy;
(c) $C_1$–$C_{22}$ alkyl either unsubstituted or substituted by a substituent chosen from (i) halogen, (ii) carboxy, (iii) $C_4$-$C_7$ monocycloalkyl, (iv) a pentatomic or hexatomic heteromonocyclic ring containing one or more heteroatoms chosen from O, N and S, and (v) unsubstituted phenyl or phenyl substituted by $C_1$-$C_4$ alkyl, $C_1$-$C_3$ alkoxy, hydroxy, halogen, tri-halo-$C_1$-$C_6$-alkyl or nitro;
(d) $C_4$-$C_7$ monocycloalkyl;
(e) a pentatomic or hexatomic heteromonocyclic ring containing one or more heteroatoms chosen from O, S and N; or
(f) unsubstituted phenyl or phenyl substituted by $C_1$-$C_4$ alkyl, $C_1$-$C_3$ alkoxy, hydroxy, halogen, tri-halo-$C_1$-$C_6$-alkyl or nitro;
(3) a group —$NHSO_2R_6$ wherein $R_6$ has one of the meanings reported above for $R_5$ except hydrogen; or
(4) the group —$N_3$;
one of $R_1$ and $R_2$ is hydrogen and the other is hydrogen, $C_1$-$C_6$ alkyl, $C_2$-$C_6$ alkenyl or $C_2$-$C_6$ alkynyl; and the symbols ---- indicate that each of (x) and (y), independently, is a single bond or a double bond, provided that R is not the group —$N_3$ when (x) is single bond and (y) is double bond.

The invention includes also the pharmaceutically acceptable salts of the compounds of formula (I) as well as all the possible isomers of formula (I), both separately and in mixture.

In the formulae of this specification a dotted line (....) indicates a substituent in the α-configuration, i.e. below the plane of the ring, a wedged line (▬) indicates a substituent in the β-configuration, i.e. above the plane of the ring, and a wavy line (~~~) indicates that a substituent may be in the α-configuration or in the β-configuration or both. Consequently, where a formula has a substituent with a wavy line bond, the formula may represent a compound having the substituent solely in the α-configuration or solely in the β-configuration, or the formula may represent a mixture of both compounds having the substituent in the α-configuration and compounds having the substituent in the β-configuration. The alkyl, alkenyl and alkynyl groups as well as the aliphatic moieties of the alkoxy groups may be branched or straight chain.

An unsubstituted $C_1$–$C_{22}$ alkyl group is, preferably, a $C_1$–$C_{17}$ alkyl group such as, for instance, methyl, ethyl, n-propyl, n-butyl, tert-butyl, n-pentyl, n-hexyl, n-heptyl, n-nonyl, n-undecyl, n-tridecyl, n-pentadecyl or n-heptadecyl.

A substituted $C_1$–$C_{22}$ alkyl group is, preferably, a $C_1$–$C_4$ alkyl, e.g. methyl, ethyl, n-propyl or tert-butyl, substituted as indicated above, preferred substituents on the said alkyl being carboxy or a $C_4$–$C_7$ monocycloalkyl or phenyl group as defined above under (c).

A $C_1$–$C_3$ alkoxy group is, preferably, methoxy or ethoxy.

A $C_1$–$C_6$ alkyl group is, preferably, a $C_1$–$C_4$ alkyl, in particular methyl, ethyl, n-propyl or tert-butyl, more preferably methyl or ethyl.

A halogen atom is, preferably, chlorine, bromine or fluorine, in particular fluorine.

A tri-halo-$C_1$–$C_6$-alkyl group is, preferably, a tri-halo methyl group, in particular trichloromethyl or trifluoromethyl.

A $C_4$–$C_7$ monocycloalkyl group is, preferably, a $C_5$–$C_7$ monocycloalkyl, in particular cyclopentyl or cyclohexyl.

A pentatomic or hexatomic heteromonocyclic ring as defined above may be either saturated or unsaturated. It is, preferably, an unsaturated pentatomic heteromonocyclic ring containing one or two heteroatoms chosen from O, S and N, in particular, for example, furyl, thienyl or imidazolyl.

A substituted phenyl is, preferably, a phenyl ring substituted by a $C_1$-$C_4$ alkyl group, in particular methyl, or by a hydroxy, methoxy, ethoxy, fluorine or trifluoromethyl group.

A $C_2$-$C_6$ alkenyl group is, preferably, $C_2$-$C_4$ alkenyl, in particular vinyl, allyl, 1-propenyl, 1-butenyl, 2-butenyl or 3-butenyl, most preferably vinyl or allyl.

A $C_2$-$C_6$ alkynyl group is, preferably, $C_2$-$C_4$ alkynyl, in particular ethynyl, 1-propynyl, 2-propynyl, 1-butynyl, 2-butynyl or 3-butynyl.

When R is a group

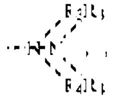

preferably each of $R_3$ and $R_4$, independently, is hydrogen or $C_1$-$C_4$ alkyl, in particular methyl or ethyl; a particularly preferred

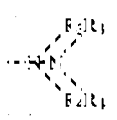

value is amino.

When R is a group —$NHCOR_5$, preferably $R_5$ is (a') hydrogen; (b') $C_1$–$C_3$ alkoxy, in particular methoxy or ethoxy, or benzyloxy, or carboxy; (c') unsubstituted $C_1$–$C_{17}$ alkyl or $C_1$–$C_4$ alkyl substituted by carboxy, $C_5$–$C_7$ monocycloalkyl or phenyl, the latter in its turn optionally substituted by $C_1$–$C_6$ alkyl, in particular methyl, or nitro; or (d') unsubstituted phenyl or phenyl substituted by $C_1$–$C_6$ alkyl, in particular methyl, or nitro.

When $R_5$ is unsubstituted $C_1$–$C_{17}$ alkyl, it is, in particular, methyl, ethyl, n-propyl, n-hexyl or n-undecyl; when $R_5$ is $C_1$–$C_4$ alkyl substituted by carboxy, it is, preferably, 2-carboxyethyl; when $R_5$ is $C_1$–$C_4$ alkyl substituted by $C_5$–$C_7$ monocycloalkyl, it is, preferably, cyclohexylmethyl, 2-cyclohexylethyl or 2-cyclopentylethyl; when $R_5$ is $C_1$–$C_4$ alkyl substituted by phenyl, it is, preferably, phenylmethyl; when $R_5$ is phenyl substituted by $C_1$–$C_6$ alkyl, it is, preferably, p-tolyl.

Particularly preferred values of R, when —$NHCOR_5$, are formylamino, benzyloxycarbonylamino, ethoxycarbonylamino, oxaloamino, acetylamino, propionylamino, butyrylamino, pivaloylamino, hexanoylamino, heptanoylamino, octanoylamino, decanoylamino, dodecanoylamino, tetradecanoylamino, hexadecanoylamino, octadecanoylamino, 3-carboxypropionylamino, 3-cyclopentyl-propionylamino, 3-cyclohexyl-propionylamino, cyclohexyl-acetylamino, phenyl-acetylamino and benzoylamino.

When R is a group —$NHSO_2R_6$, preferably $R_6$ is unsubstituted $C_1$–$C_4$ alkyl, in particular methyl or ethyl, or phenyl either unsubstituted or substituted by $C_1$–$C_6$ alkyl, in particular methyl, or by nitro.

Particularly preferred values of R, when —$NHSO_2R_6$, are methanesulfonylamino, ethanesulfonylamino and p-toluenesulfonylamino.

Preferably in the formula (I) either R is a group

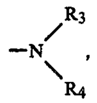

where in $R_3$ and $R_4$ are as defined above, or, subject to the above proviso, R is the group —$N_3$.

As already said, the invention includes also the pharmaceutically acceptable salts of the compounds of formula (I). Preferred salts according to the invention are the salts of the compounds of formula (I) wherein R is a group

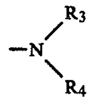

as defined above with pharmaceutically acceptable acids, both inorganic acids such as, e.g., hydrochloric, sulfuric or phosphoric acid, and organic acids such as, e.g., citric, fumaric, maleic, malic, ascorbic, tartaric, benzoic, acetic, phenylacetic, cyclohexylacetic, 3-cyclohexylpropionic, methanesulfonic, ethanesulfonic, benzenesulfonic, p-toluenesulfonic or p-nitrobenzenesulfonic acid.

Also the quaternary ammonium salts and hydroxides of the compounds of formula (I) wherein R is

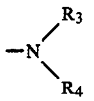

are within the scope of the invention: they are, for instance, quaternary alkyl, e.g. methyl, ethyl or cetyl, ammonium salts, e.g. iodides, bromides or chlorides, or hydroxides. Though the above indicated salts are the preferred ones according to the invention, nevertheless this is meant to include also other salts, e.g. the pharmaceutically acceptable salts of the compounds of formula (I) containing an acidic, i.e. carboxy, group with pharmaceutically acceptable bases.

These may be both inorganic bases such as, for instance, alkali metal, e.g. sodium or potassium, or alkaline earth metal, e.g. calcium or magnesium, hydroxides, and organic bases such as, for instance, alkyl amines, e.g. methylamine or triethylamine, aralkylamines, e.g. benzylamine, dibenzylamine, α- or β-phenylethylamine, or heterocyclic amines such as, e.g., piperidine, 1-methyl-piperidine, piperazine or morpholine.

A particularly preferred class of compounds according to the invention are the compounds of formula (I) wherein R is a group

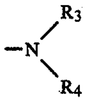

wherein one of $R_3$ and $R_4$ is hydrogen and the other is, independently, hydrogen or unsubstituted $C_1$–$C_{22}$ alkyl; one of $R_1$ and $R_2$ is hydrogen and the other is hydrogen, $C_1$–$C_6$ alkyl, $C_2$–$C_6$ alkenyl or $C_2$–$C_6$ alkynyl; the symbol ---- indicates that each of (x) and (y), independently; is a single bond or a double bond, and the pharmaceutically acceptable salts thereof.

In the said particularly preferred class, an unsubstituted $C_1$–$C_{22}$ alkyl is, preferably, $C_1$–$C_4$ alkyl, in particular methyl or ethyl; a $C_1$–$C_6$ alkyl group is, preferably, $C_1$–$C_4$ alkyl, in particular methyl or ethyl; a $C_2$–$C_6$ alkenyl group is, preferably, $C_2$–$C_4$ alkenyl, in particular vinyl; a $C_2$–$C_6$ alkynyl group is, preferably, $C_2$–$C_4$ alkynyl, in particular ethynyl or 2-propynyl. Preferably R is amino, methylamino or ethylamino, especially amino, and, preferably, one of $R_1$ and $R_2$ is hydrogen and the other is hydrogen, methyl, ethyl, ethynyl or 2-propynyl.

Another particularly preferred class of compounds according to the invention are the compounds of formula (I) wherein R is the group —$N_3$; one of $R_1$ and $R_2$ is hydrogen and the other is hydrogen or $C_1$–$C_6$ alkyl, and either (x) and (y) are both single bonds or both double bonds, or (x) is double bond and (y) is single bond.

In the hereabove said particularly preferred class a $C_1$–$C_6$ alkyl is, preferably, $C_1$–$C_4$ alkyl, in particular methyl or ethyl.

Most preferably $R_1$ and $R_2$ are both hydrogen.

Examples of specific compounds preferred under the invention are:

4-azidoandrost-4-en-3,17-dione;
4-azidoandrosta-1,4-dien-3,17-dione;
4-azidoandrosta-1,4,6-trien-3,17-dione;
4-aminoandrost-4-en-3,17-dione;

4-aminoandrosta-4,6-dien-3,17-dione;
4-amino-6-methylandrosta-4,6-dien-3,17-dione;
4-amino-7-methylandrosta-4,6-dien-3,17-dione;
4-aminoandrosta-1,4,6-trien-3,17-dione;
4-amino-6-methylandrosta-1,4,6-trien-3,17-dione;
4-amino-7-methylandrosta-1,4,6-trien-3,17-dione;
4-amino-7-ethynylandrosta-4,6-dien-3,17-dione;
4-amino-7-(2-propynyl)androsta-4,6-dien-3,17-dione;
and, when appropriate, the pharmaceutically acceptable salts thereof.

The compounds of the invention may be prepared by a process comprising:

(A) reacting a compound of formula (II) or (IIa)

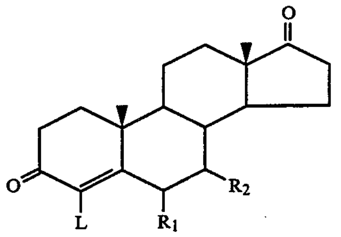

(II)

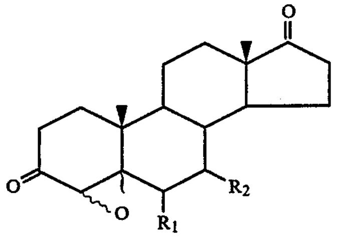

(IIa)

wherein $R_1$ and $R_2$ are as defined above and L is a leaving group displaceable by nucleophilic substitution, with a compound of formula (III)

$M—N_3$ (III)

wherein M is an alkali metal or ammonium cation, or a tri-$C_1$-$C_6$-alkylsilyl group, so obtaining, according to the reaction conditions, either a compound of formula (I) wherein R is the group $—N_3$ and (x) and (y) are both single bonds, or a compound of formula (I) wherein R is a group

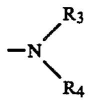

wherein $R_3$ and $R_4$ are both hydrogen, (x) is single bond and (y) is double bond; or (B) reacting a compound of formula (IV)

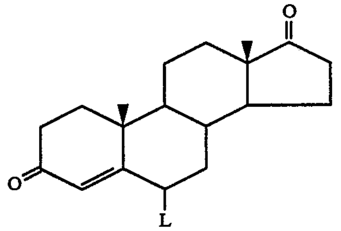

(IV)

wherein L has the meaning reported above, with a compound of formula (III), so obtaining, according to the reaction conditions, either a compound of formula (I) wherein R is the group $—N_3$, (x) and (y) are both single bonds and $R_1$ and $R_2$ are both hydrogen, or a compound of formula (I) wherein R is a group

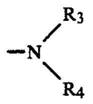

wherein $R_3$ and $R_4$ are both hydrogen, (x) is single bond, (y) is double bond, and $R_1$ and $R_2$ are both hydrogen; or (C) reacting a compound of formula (V)

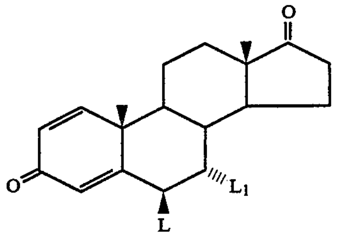

(V)

wherein each of L and $L_1$, which may be the same or different, is a leaving group displaceable by nucleophilic substitution, with a compound of formula (III), so obtaining a compound of formula (I) wherein R is the group $—N_3$, (x) and (y) are both double bonds, and $R_1$ and $R_2$ are both hydrogen; or (D) reacting a compound of formula (VI) or (VIa)

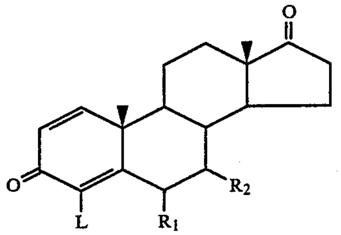

(VI)

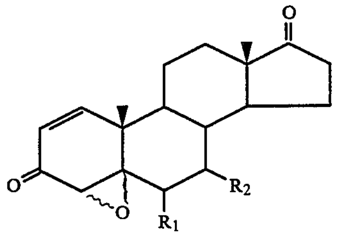

(VIa)

wherein L, $R_1$ and $R_2$ are as defined above, with a compound of formula (III), so obtaining a compound of formula (I) wherein R in the group $—N_3$, (x) is double bond and (y) is single bond; or (E) pyrolysing a compound of formula (I) wherein R is the group $—N_3$ and (x) and (y) are both single bonds, so obtaining a compound of formula (I) wherein R is a group

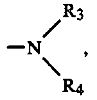

wherein $R_3$ and $R_4$ are both hydrogen, (x) is single bond and (y) is double bond; or (F) reducing a compound of formula (I) wherein R is the group $—N_3$, so obtaining a compound of formula (I) wherein R is a group

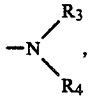

wherein $R_3$ and $R_4$ are both hydrogen, and, if desired, in any order, alkylating a compound of formula (I) wherein R is a group

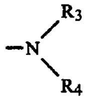

wherein $R_3$ and $R_4$ are both hydrogen to obtain a corresponding compound of formula (I) wherein R is a group

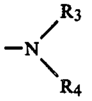

wherein at least one of $R_3$ and $R_4$ is $C_1$–$C_{22}$ alkyl, or acylating a compound of formula (I) wherein R is a group

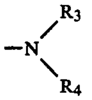

wherein $R_3$ and $R_4$ are both hydrogen, to obtain a corresponding compound of formula (I) wherein R is a group $—NHCOR_5$ or a group $—NHSO_2R_6$ wherein $R_5$ and $R_6$ are as defined above, and/or, if desired, reducing a compound of formula (I) wherein (x) is single bond and (y) is double bond to obtain a corresponding compound of formula (I) wherein (x) and (y) are both single bonds and/or, if desired, oxidizing a compound of formula (I) wherein (x) is single bond and R is different from $—N_3$, to obtain a corresponding compound of formula (I) wherein (x) is double bond and/or, if desired, converting a compound of formula (I) into another compound of formula (I) and/or, if desired, salifying a compound of formula (I) or obtaining a free compound of formula (I) from a salt thereof and/or, if desired, separating a mixture of isomers of formula (I) into the single isomers.

All over the present description, when unspecified, a substituent is meant to have all the meanings indicated with reference to the broadest formula (I), and the same is meant with the wording "as defined above".

The leaving group L in the compounds of formula (II), (IV), (V) and (VI), as well as the leaving group $L_1$ in the compounds of formula (V), may be a halogen atom or the residue of a reactive ester, either sulfonic acid ester or carboxylic acid ester, of an alcohol.

When L or $L_1$ is halogen, iodine, bromine and chlorine are preferred.

When L or $L_1$ is an ester residue as defined above, it is, preferably, a group $R_7SO_2—O—$ wherein $R_7$ is methyl, trifluoromethyl, p-tolyl- or p-nitrophenyl, or a group $R_8—COO—$ wherein $R_8$ is methyl, trifluoromethyl or p-nitrophenyl. When M in the compound of formula (III) is an alkali metal cation, this is preferably a sodium or lithium cation. When M is a tri-$C_1$–$C_6$-alkylsilyl group, trimethylsilyl and dimethyltert.butylsilyl are preferred.

Accordingly, preferred compounds of formula (III) are sodium azide, lithium azide, ammonium azide, trimethylsilylazide and dimethyltert.butylsilylazide.

The reaction between a compound of formula (II) or (IIa) and a compound of formula (III) is preferably carried out in an organic solvent such as, for instance, N,N-dimethylformamide, N,N-dimethylacetamide or dimethylsulfoxide; some water or an aqueous alcoholic, e.g. methanolic or ethanolic, solution may be added, if desired, to increase the solubility of the azide of formula (III).

If the reaction is performed under mild conditions, such as, for instance, at low temperature, e.g. from about 0° C. to about 60° C., and for short reaction times, e.g. from some minutes to about 1 hour, a compound of formula (I) wherein R is the group $—N_3$, and (x) and (y) are both single bonds is obtained.

If, on the contrary, the reaction is performed under more drastic conditions, for instance at higher temperature, e.g. from about 60° C. to about 150° C., and for longer reaction times, e.g. from 30 minutes to several hours, then a compound of formula (I) is obtained wherein R is a group

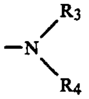

wherein $R_3$ and $R_4$ are both hydrogen, (x) is a single bond and (y) is a double bond. The reaction between a compound of formula (IV) and a compound of formula (III) may be carried out in analogous way as described hereabove for the reaction between the compounds (II), or (IIa), and (III).

In analogous fashion, mild reaction conditions, as those indicated for the previous reaction, lead to a compound of formula (I) wherein R is the group $—N_3$, (x) and (y) are both single bonds and $R_1$ and $R_2$ are both hydrogen; more drastic conditions such as, e.g., those described before for the analogous reaction, lead to a compound of formula (I) wherein R is a group

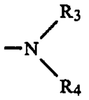

wherein $R_3$ and $R_4$ are both hydrogen (x) is single bond, (y) is double bond and $R_1$ and $R_2$ are both hydrogen.

Preferably in the above formula (V) either L and $L_1$ are the same halogen, especially bromine, chlorine or iodine, or L is halogen, in particular bromine or iodine, and $L_1$ is a group $R_8$—COO— wherein $R_8$ is as defined above, preferably methyl.

The reaction between a compound of formula (V) and a compound of formula (III) may be carried out in analogous way as described hereabove for the reaction between a compound (III) and, respectively, a compound (II), (IIa) or (IV). In this case both mild and drastic reaction conditions lead to the same compound of formula (I) wherein R is the group —$N_3$, (x) and (y) are both double bonds and $R_1$ and $R_2$ are both hydrogen.

The reaction between a compound of formula (VI) or (VIa) and a compound of formula (III) may be carried out in analogous way as described hereabove for the reaction between a compound (III) and, respectively, a compound of formula (II), (IIa), (IV) or (V). Also in this case both mild and drastic conditions lead to a same compound, which is a compound of formula (I) wherein R is the group —$N_3$, (x) is double bond and (y) is single bond.

The pyrolysis of a compound of formula (I) wherein R is the group —$N_3$ and (x) and (y) are both single bonds, to give a corresponding compound of formula (I) wherein R is a group

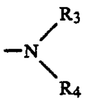

wherein $R_3$ and $R_4$ are both hydrogen, (x) is single bond and (y) is double bond, may be, e.g., carried out by heating at a temperature of 100°-150° C., for some minutes to several hours, in a suitable medium such as, for instance, N-N-dimethylformamide, N,N-dimethylacetamide or dimethylsulfoxide, or their aqueous mixtures, in the presence of a weak base such as, e.g., $NaN_3$, $LiN_3$, triethylamine, collidine and the like.

In particular, for example, if desired, a 4-azido compound of formula (I) wherein (x) and (y) are both single bonds obtained from the above described reactions between a compound of formula (III) and, respectively, a compound of formula (II), (IIa) or (IV), under mild reaction conditions, may be first isolated and then converted to the corresponding 4-amino compound of formula (I) wherein (x) is single bond and (y) is double bond by pyrolysis as hereinbefore indicated. The reduction of a compound of formula (I) wherein R is the group —$N_3$ to give a compound of formula (I) wherein R is a group

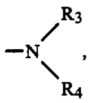, wherein $R_3$ and $R_4$ are both hydrogen may be carried out following known methods, for example with a variety of reducing agents, e.g. propane-1,3-dithiol in triethylamine [Tetr. Lett. 39, 3633 (1978)], dithiolthreitol in aqueous solutions, mercaptoacetic acid and triethylamine, or, for instance, catalytic reductions using, e.g., palladium catalysts.

The alkylation of a compound of formula (I) wherein R is a group

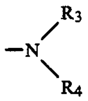

wherein $R_3$ and $R_4$ are both hydrogen to obtain a corresponding compound of formula (I) wherein R is a group

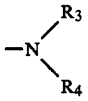

wherein at least one of $R_3$ and $R_4$ is $C_1$-$C_{22}$ alkyl, may be carried out by reaction with a suitable alkylating agent which may be e.g., a $C_1$-$C_{22}$ alkyl halide, in particular iodide, or di-alkyl sulfate; for obtaining a compound of formula (I) wherein R is a group

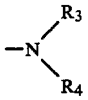

wherein at least one of $R_3$ and $R_4$ is methyl or ethyl suitable alkylating agents are, e.g., methyl iodide, dimethylsulfate or, respectively, ethyliodide and diethylsulfate. Reaction conditions well known to the skilled in the art and well described in the organic chemistry may be followed: see, e.g., Lucier et al, Org. Synth. 44, 72 (1964). The acylation of a compound of formula (I) wherein R is a group

wherein $R_3$ and $R_4$ are both hydrogen to obtain a corresponding compound of formula (I) wherein R is a group —$NHCOR_5$ or —$NHSO_2R_6$ may be performed using an appropriate acylating agent carrying the desired —$COR_5$ or, respectively, —$SO_2R_6$ moiety.

Thus, for example, in order to obtain a compound of formula (I) wherein R is a group —$NHCOR_5$ wherein $R_5$ is as defined above under (c), (d), (e) and (f) a suitable acylating agent may be a carboxylic acid of formula $R_5$—COOH, wherein $R_5$ is as hereinbefore indicated, or, preferably, a reactive derivative thereof such as, for instance, an halide, in particular the chloride, or the anhydride or a mixed anhydride thereof. Similar acylating agents may be used for obtaining compounds of formula (I) wherein R is a group —$NHCOR_5$ wherein $R_5$ is as defined under (a) and (b); for example an oxalohalide, e.g. chloride, may be useful to prepare a compound of formula (I) wherein R is a group —$NHCOR_5$ wherein $R_5$ is carboxy, and a $C_1$-$C_3$ alkyl-chlorocarbonate or benzylchlorocarbonate may be used for obtaining a compound of formula (I) wherein R is a group —$NHCOR_5$ wherein $R_5$ is $C_1$-$C_3$ alkoxy or, respectively, benzyloxy.

Suitable acylating agent for obtaining a compound of formula (I) wherein R is a group —$NHSO_2R_6$ may be, e.g., the appropriate sulfonic acid of formula $R_6SO_3H$ or, preferably, a derivative thereof such as, for instance, a corresponding sulfonyl halide, e.g. chloride, or anhydride.

When the acylation reaction proceeds through elimination of an acid component, the presence of a base, preferably an organic base such as, e.g., triethylamine or pyridine, is generally required; when the base is pyridine, this may also function as solvent; otherwise any appropriate inert, preferably anhydrous, solvent may be employed such as, e.g., toluene, benzene, dioxane, tetrahydrofurane, N,N-dimethylformamide or dimethylsulfoxide.

The reaction temperature may vary, e.g., between about 0° C. and about 100° C. and the reaction times may be, e.g., from about one hour to about 48 hours.

The reduction of a compound of formula (I) wherein (x) is single bond and (y) is double bond to obtain the corresponding compound of formula (I) wherein (x) and (y) are both single bonds, may be performed according to known methods, for example with lithium and ammonia in an anhydrous solvent such as e.g., diethyl ether, dioxane or tetrahydrofurane, at a temperature from about −70° C. to about −40° C. in accordance with the procedure described by J. A. Campbell and J. C. Babcock in J. Am. Chem. Soc. 81, 4069 (1959).

The oxidation of a compound of formula (I) wherein (x) is single bond and R is different from $-N_3$, to obtain a corresponding compound of formula (I) wherein (x) is double bond may be carried out with any appropriate oxidizing agent; for example 2,3-dichloro-5,6-dicyanobenzoquinone (DDQ) may be used operating in an anhydrous inert solvent such as, e.g., benzene, at reflux temperature, or alternatively, selenium dioxide may also be employed following conventional procedures.

Optional conversions of a compound of formula (I) into another compound of formula (I) include, for example, the conversion of a compound of formula (I) wherein R is a group $-NHCOR_5$ or $-NHSO_2R_6$, wherein $R_5$ and $R_6$ are as defined above, into the corresponding compound of formula (I) wherein R is a group

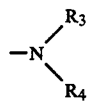

wherein $R_3$ and $R_4$ are both hydrogen.

The latter conversion may be carried out by known methods, for example by treatment with a basic agent, for instance an alkali metal hydroxide or carbonate such as, e.g., NaOH, KOH, LiOH, $Na_2CO_3$ or $K_2CO_3$, in water or in an aqueous organic solvent chosen, e.g., from an aliphatic alcohol, e.g. methanol or ethanol, acetone, tetrahydrofurane or dioxane, at a temperature from, e.g., the room temperature to about 100° C. and for reaction times which may vary, e.g., from about one hour to about 48 hours.

Conventional methods may be used for salifying a compound of formula (I) and for obtaining a free compound of formula (I) from a salt thereof, and standard procedures, such as, e.g., fractional crystallization and chromatography, may be followed as well for separating a mixture of isomers of formula (I) into the single isomers.

A compound of formula (II) wherein the leaving group L is a halogen atom may be obtained halogenating a compound of formula (VII)

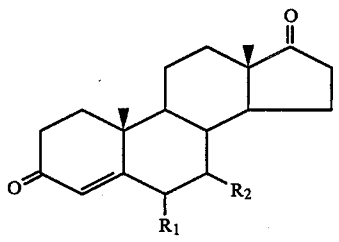

(VII)

wherein $R_1$ and $R_2$ are as defined above.

The halogenation may be carried out in a known way, for example using thionyl or sulfonyl chloride as the halogenating agent, and operating, e.g., in pyridine at a temperature from about 0° C. to about 50° C. in accordance with the procedure described by N. Sugimoto et al in Chem. Pharm. Bull. (Tokyo) 10, 427 (1962).

A compound of formula (II) wherein the leaving group L is the residue of a reactive ester of an alcohol as defined above may be obtained esterifying a compound of formula (VIII)

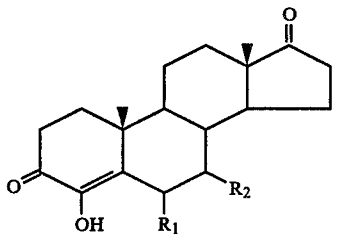

(VIII)

wherein $R_1$ and $R_2$ are as defined above, with the desired sulfonic or carboxylic acid, e.g. a sulfonic acid of formula $R_7SO_3H$ or a carboxylic acid of formula $R_8COOH$ wherein $R_7$ and $R_8$ are as defined above, or, preferably, with a reactive derivative of the said acids, in particular, e.g., a corresponding halide, preferably chloride, or anhydride.

The esterification reaction may be performed according to the usual methods described in the organic chemistry for this kind of reaction following standard procedures.

A compound of formula (IIa) may be obtained by epoxidizing a corresponding compound of formula (VII).

The epoxidation may be carried out by treatment with a suitable oxidizing agent, preferably concentrated, e.g. 36%, $H_2O_2$, in an alcoholic, e.g. methanolic or ethanolic, alkali metal, e.g. sodium or potassium, hydroxide solution. Reaction conditions well known to the skilled in the art and well described in the organic chemistry may be followed. An alternative way for obtaining a compound of formula (II) wherein L is halogen may be to treat a compound of formula (IIa) with a halohydric acid, e.g. HCl or HBr. The reaction may be performed following known procedures, for example operating in a solvent chosen, e.g., from chloroform, dichloromethane, tetrachloromethane, dichloroethane or glacial acetic acid at room temperature, according to the procedure described by B. Camerino et al in Il Farmaco Ed. Sci. 11, 586 (1956).

A compound of formula (IV) wherein L is halogen may be prepared halogenating a compound of formula (IX)

(IX)

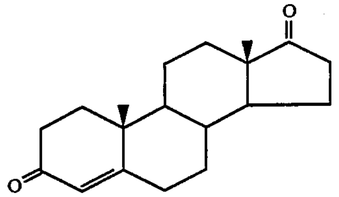

according to known methods, for example by treatment with a N-halosuccinimide or acetamide, e.g. N-bromosuccinimide or N-bromoacetamide, in a halogenated organic solvent such as, e.g., carbon tetrachloride, in accordance with the procedure described by Djerassi et al in J. Am. Chem. Soc. 72, 4534 (1950).

The compounds of formula (IV) wherein L is the residue of a reactive ester of an alcohol as defined above are known compounds or may be prepared by known methods from known compounds, and the same is for the compounds of formula (V). In particular, for example, a compound of formula (V) wherein L and $L_1$ are the same halogen, may be prepared halogenating a compound of formula (X)

(X)

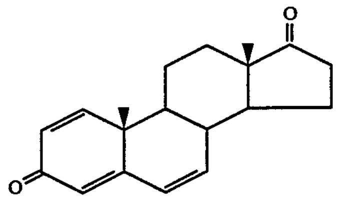

according to known methods, for example by treatment with bromine or iodine in acetic acid.

A compound of formula (V) wherein L is halogen, e.g. bromine or iodine, and $L_1$ is an ester residue, e.g. a group $R_8$—COO— as defined above, may be prepared by acylating a compound of formula (XI)

(XI)

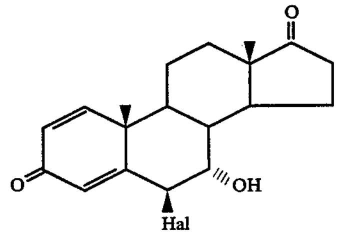

wherein Hal is halogen, e.g. bromine or iodine, according to known methods.

The compounds of formula (VI) and (VIa) may be prepared in analogous way as described before for the preparation of the similar compounds of formula (II) and, respectively, (IIa). In particular, e.g., a compound of formula (VIa) may be prepared by epoxidation of a compound of formula (XII)

(XII)

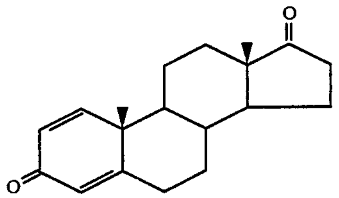

following a procedure analogous to that described above for the epoxidation of a compound of formula (VII).

The compounds having the formulae (III), (VII), (VIII), (IX), (X), (XI) and (XII) are known compounds or may be prepared by known methods from known compounds. In particular, for instance, the compounds of formula (VIII) may be prepared following the procedure described by B. Camerino et al in Il Farmaco 7, 19 (1956).

The compounds of the present invention are inhibitors of the biotransformation of endogenous androgens, i.e. they are steroidal aromatase inhibitors.

Aromatase (estrogen synthetase) is the enzyme responsible for the final step in biosynthesis of estrogens: the conversion of androgens to estrogens, e.g. of androstendione and testosterone to estrone and estradiol respectively. The aromatase is a microsomal P450 enzyme complex which acts on the androgenic substrate.

Since the products of aromatase action, i.e. estrogens, are responsible of the growth of hormone-dependent tumours, the aromatase inhibitors compounds of the invention can find use for the treatment of the said tumours.

In view of the above, the compounds of the invention can be useful as an alternative to endocrine ablation, e.g. oophorectomy, hypophysectomy or adrenalectomy, in the treatment of advanced hormone-dependent tumours, e.g. breast, pancreatic, endometrial and ovarian cancers, especially breast cancer.

The aromatase inhibitors for formula (I) can find also use in the control of reproduction: indeed a decrease in oestrogen levels in vivo results in gonad-inhibiting activity and in insufficient uterine development; aromatase inhibitors may be at the same time implantation inhibitors. Another application of the compounds of the invention is in the treatment of prostatic hypertrophy or hyperplasia, related to an excessive oestrogen production and the shifting of the oestrogen/androgen ratio to higher values. Furthermore, the compounds of the invention, producing decrease in estradiol formation, may be useful for the treatment of male fertility disturbances (Drugs 28: 263, 1984). It is known indeed that estradiol may play a role in regulating spermatogenesis and may also indirectly inhibit spermatogenesis by preventing the Leidig cells from maximally producing testosterone in response to LH. Accordingly, decreased estradiol formation, as can be obtained through administration of the compounds of the invention, leads to an improvement of both sperm count and fertility, in patients with infertility due to oligozoospermia. Aromatase inhibition by the compounds of the present invention was determined, e.g., both in vitro (human placental aromatase) and in vivo (ovarian aromatase activity) in rats. As an example, the activity of 4-aminoandrosta-4,6-dien-3,17-dione (internal code FCE 24210) was compared to that of the well-known aromatase inhibitors 4-hydroxyandrost-4-en-3,17-dione (4OH-A), $\Delta^1$-testololactone and androsta-1,4-dien-3,17-dione [A. M. H. Brodie, Cancer Research (Suppl.) 42, 3312 s, (1982); D. F. Covey and W. F. Hood, Cancer Research (Suppl.) 42, 3327 s (1982)].

The following test procedures were followed.

(a) Aromatase inhibition in vitro

The enzyme system was isolated from the microsomal fraction of human placental tissue according to standard procedure. The assay of Thompson and Siiteri [E. A. Thompson and P. K. Siiteri, J. Biol. Chem. 249, 5364, (1974)] which determines the rate of aromatization as measured by the liberation of $^3H_2O$ from 4-[1β,2β-$^3$H] androsten-3,17-dione was used. All incubations were carried out in a shaking water bath at 37° C. in air in 10 mM potassium phosphate buffer, pH 7.5, which contained 100 mM KCl, 1 mM EDA and 1 mM dithiothreitol. The experiments were carried out in 1 ml incubation volume containing 50 nM 4-[$^3$M]androstendione, various concentrations of the inhibitors, 100 μM NADPH and 0.05 mg of microsomal proteins. After 15 minutes of incubation the reaction was stopped by the addition of chloroform (5 ml). After centrifugation at 1500×g for 5 minutes, aliquots (0.5 ml) were removed from the water phase for determination of $^3H_2O$ formed. The concentration of each compound required to reduce control aromatase by 50% ($IC_{50}$) was determined by plotting % inhibition versus log of inhibitor concentration. The relative potency of each compound versus 4 OH-A was calculated according to the relation:

$$\text{Relative potency} = \frac{IC_{50} \text{ of 4 OH—A}}{IC_{50} \text{ of test compound}}$$

(b) Aromatase inhibition in vivo in rats

Adult female rats were twice treated subcutaneously with 100 I.U. pregnant mares' serum gonadotropin (PMSG) at 4 days' interval, in order to increase ovarian aromatase activity, according to Brodie's procedure [A. M. H. Brodie et al., Steroids 38, 693, (1981)]. Three days after the second PMSG treatment, groups of 6 animals each were given orally the vehicle (0.5% methocel) or the inhibitor at 30 mg/kg. Animals were killed 24 hours later, microsomes were isolated from ovaries and their aromatase activity determined using a method similar to that described in (a). The incubations were carried out for 30 minutes in 1 ml incubation volume containing 0.1 mg of microsomal proteins, 100 nM 4-[$^3$H]androstendione and 100 μM NADPH. % inhibition of control aromatase activity was calculated. The obtained data are reported in the following table.

TABLE

Inhibition of human placental aromatase in vitro and of rat ovarian aromatase in vivo

| | IN VITRO | | IN VIVO |
|---|---|---|---|
| Compound | $IC_{50}$ nM | (Relative potency) | % Aromatase inhibition at 30 mg/kg p.o. |
| 4-hydroxyandrost-4-en-3,17-dione (4-OH-A) | 44 | (1.00) by definition | inactive |
| $\Delta^1$-testololactone (testolactone) | 8240 | (0.005) | inactive |
| androsta-1,4-dien-3,17-dione | 112 | (0.39) | 37 |

TABLE-continued

Inhibition of human placental aromatase in vitro and of rat ovarian aromatase in vivo

| | IN VITRO | | IN VIVO |
|---|---|---|---|
| Compound | $IC_{50}$ nM | (Relative potency) | % Aromatase inhibition at 30 mg/kg p.o. |
| 4-aminoandrosta-4,6-dien-3,17-dione (FCE 24210) | 148 | (0.30) | 70 |

The tabulated data indicate that the compounds of the invention, e.g. 4-aminoandrosta-4,6-dien-3,17-dione (FCE 24210), are very potent aromatase inhibitors both in vitro and in vivo. In vivo the new compound FCE 24210 is found to be about equipotent as androsta-1,4-dien-3,17-dione and about 55 times more potent than $\Delta^1$-testololactone.

Although its in vitro potency is about three times lower than that of 4-OH-A, the new compound is, however, very effective when administered in vivo by oral route, as a consequence of an unusual resistance to hepatic metabolization, while 4-OH-A is ineffective at the same dose (30 mg/kg). In fact, the major disadvantage for the therapeutical use of 4-OH-A as antitumor agent in women is the need of parenteral administration, the compound being extensively conjugated after oral administration [R. C. Coombes et al., Lancet II, 1237, (1984)].

On the other hand, the in vivo activity of the compound FCE 24210 is also very superior to that of androsta-1,4-dien-3,17-dione.

In view of their high therapeutic index, the compounds of the invention can be used safely in medicine. For example, the acute toxicity ($LD_{50}$) of the compounds of the invention in the mouse, determined by single administration of increasing doses and measured on the seventh day after oral treatment was found to be negligible.

The compounds of the invention can be administered in a variety of dosage forms, e.g. orally, in the form of tablets, capsules, sugar or film coated tablets, liquid solutions or suspensions; rectally, in the form of suppositories; parenterally, e.g. intramuscularly, or by intravenous injection or infusion. The dosage depends on the age, weight, conditions of the patient and administration route; for example the dosage adopted for oral administration to adult humans, e.g. for the representative compound of the invention FCE 24210, may range from about 10 to about 150–200 mg pro dose, from 1 to 5 times daily.

The invention includes pharmaceutical compositions comprising a compound of the invention in association with a pharmaceutically acceptable excipient, which can be a carrier or diluent.

The pharmaceutical compositions containing the compounds of the invention are usually prepared following conventional methods and are administered in a pharmaceutically suitable form.

For example, the solid oral forms may contain, together with the active compound, diluents, e.g., lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disaggregating agents, e.g. a starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration may be e.g. syrups, emulsions and suspensions.

The syrups may contain as carrier, for example, saccharose or saccharose with glycerine and/or mannitol and/or sorbitol. The suspensions and the emulsions may contain as carrier, for example, a natural gum, agar, sodium alginate, pectin, methylcellulose, carboxymethylcellulose, or polyvinyl alcohol.

The suspensions or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride.

The solutions for intravenous injections or infusions may contain as carrier, for example, sterile water or, preferably, they may be in the form of sterile, aqueous, isotonic saline solutions.

The suppositories may contain together with the active compound a pharmaceutically acceptable carrier, e.g. cocoa-butter, polyethylene glycol, a polyoxyethylene sorbitan fatty acid ester surfactant or lecithin.

The following examples illustrate but do not limit the invention.

EXAMPLE 1

4-aminoandrosta-4,6-dien-3,17-dione [I, $R=NH_2$, $R_1=R_2=H$, (x)=single bond, (y)=double bond]

To a stirred solution of 4.98 g of 4-methanesulfonyloxyandrost-4-en-3,17-dione in 250 ml of dimethylformamide are added 1.1 g of powdered sodium azide dissolved in 14 ml of water. The resulting mixture is heated to 100° C. for 90 minutes. The cooled mixture is then added to 1 l of water with external cooling and extracted with ethyl acetate (4×250 ml). The combined extracts are thoroughly washed with saturated sodium chloride aqueous solution, dried and evaporated in vacuo to yield a crude product, which is purified by column chromatography on neutral $Al_2O_3$.

Elution with n-hexane:ethyl acetate 1:1 to ethyl acetate yields the title compound as a yellow solid, m.p. 148°-150° C. (dec.); $[\alpha]_D=+199.1°$ (c=1, $CHCl_3$);

U.V. (95% EtOH): $\lambda max=347$ nm, $\epsilon=12,395$;

N.M.R. ($CDCl_3$) δ: 0.87 (3H, s); 1.00 (3H, s); 4.45 (2H, bs); 6.01 (1H, dd); 6.40 (1H, dd).

By proceeding analogously, the following compounds are prepared:

4-amino-6-methylandrosta-4,6-dien-3,17-dione;
4-amino-7-methylandrosta-4,6-dien-3,17-dione;
4-amino-7-ethynylandrosta-4,6-dien-3,17-dione;
4-amino-7-(2-propynyl)androsta-4,6-dien-3,17-dione;
4-amino-7-ethylandrosta-4,6-dien-3,17-dione;
4-amino-7-(1-propynyl)androsta-4,6-dien-3,17-dione;
4-amino-7-vinylandrosta-4,6-dien-3,17-dione;
4-amino-7-(1-butynyl)androsta-4,6-dien-3,17-dione;
4-amino-7-(2-butynyl)androsta-4,6-dien-3,17-dione; and
4-amino-7-(3-butynyl)androsta-4,6-dien-3,17-dione.

EXAMPLE 2

4-aminoandrosta-4,6-dien-3,17-dione [I, $R=NH_2$, $R_1=R_2=H$, (x)=single bond, (y)=double bond]

To a stirred solution of 6.04 g of 4,5-epoxyandrosta-3,17-dione in 100 ml of dimethylsulphoxide and 1.5 ml of concentrated $H_2SO_4$ are added 20.8 g of powdered sodium azide. The resulting mixture is heated at 100° C. for 1 hour, cooled and poured into 1000 ml of an iced 3% HCl aqueous solution. After 15 minutes stirring, the mixture is filtered, washed with diethyl ether and brought to pH 9 by addition of a 2N NaOH aqueous solution. The resulting precipitate is filtered off, washed with water and dried in vacuo at 50° C. There are obtained 4.5 g of the title compound, m.p. 148°-150° C. (dec.).

By proceeding analogously, the following compounds are prepared:

4-amino-6-methylandrosta-4,6-dien-3,17-dione;
4-amino-7-methylandrosta-4,6-dien-3,17-dione;
4-amino-7-ethynylandrosta-4,6-dien-3,17-dione;
4-amino-7-(2-propynyl)androsta-4,6-dien-3,17-dione;
4-amino-7-ethylandrosta-4,6-dien-3,17-dione;
4-amino-7-(1-propynyl)androsta-4,6-dien-3,17-dione;
4-amino-7-vinylandrosta-4,6-dien-3,17-dione;
4-amino-7-(1-butynyl)androsta-4,6-dien-3,17-dione;
4-amino-7-(2-butynyl)androsta-4,6-dien-3,17-dione; and
4-amino-7-(3-butynyl)androsta-4,6-dien-3,17-dione.

EXAMPLE 3

4-azidoandrost-4-en-3,17-dione [I, $R=N_3$, $R_1=R_2=H$, (x)=(y)=single bond]

To a stirred solution of 1.0 g of 4-methanesulfonyloxyandrost-4-en-3,17-dione in 5 ml of dimethylformamide are added 220 mg of powdered sodium azide dissolved in 3 ml of water. The resulting mixture is heated at 60° C. for 1 hour, cooled, poured into 250 ml of cold water and extracted with ethyl acetate (4×50 ml). The combined extracts are washed with saturated NaCl aqueous solution, dried over $Na_2SO_4$ and evaporated in vacuo to yield a residue which is purified by flash column chromatography on neutral $Al_2O_3$. Elution with n-hexane:diethyl ether 1:1 gives 0.52 g of the title compound, m.p. 142°-143° C.

U.V. (95% EtOH) $\lambda_{max}=284$ nm, $\epsilon=9,855$;

I.R. (Nujol): $\nu_{max}=2100, 1730, 1670, 1590$ $cm^{-1}$;

N.M.R. ($CDCl_3$+DMSO, δ): 0.91 (3H, s); 1.21 (3H, s); 3.10 (1H, s).

EXAMPLE 4

4-azidoandrost-4-en-3,17-dione [I, $R=N_3$, $R_1=R_2=H$, (x)=(y)=single bond]

To a stirred solution of 1.5 g of 4,5-epoxyandrosta-3,17-dione in 26 ml of dimethylsulphoxide and 0.35 ml of concentrated sulphuric acid are added 5.2 g of powdered sodium azide. The resulting mixture is heated at 40° C. for 40 minutes, cooled, poured into 250 ml of iced water and extracted with ethyl acetate (4×100 ml). The combined extracts are worked up as described in the example 3. There are obtained 1.15 g of the title compound, m.p. 142°-143° C.

EXAMPLE 5

4-aminoandrosta-4,6-dien-3,17-dione [I, R=$NH_2$, $R_1$=$R_2$=H, (x)=single bond, (y)=double bond]

To a stirred solution of 1.1 g of 6-bromoandrost-4-en-3,17-dione in 57.4 ml of dimethylformamide are added 0.250 g of sodium azide dissolved in 2 ml of water. The resulting mixture is heated at 100° C. for 90 minutes, cooled and worked up as described in the example 1. There are obtained 0.325 g of the title compound, m.p. 148°-150° C. (dec.).

EXAMPLE 6

4-azidoandrost-4-en-3,17-dione [I, R=$N_3$, $R_1$=$R_2$=H, (x)=(y)=single bond]

To a stirred solution of 1.1 g of 6-bromoandrost-4-en-3,17-dione in 57.4 ml of dimethylformamide are added 0.250 g of sodium azide. The resulting mixture is heated at 30°-35° C. for 72 hours, cooled and worked up as described in the example 3. There are obtained 0.476 g of the title compound, m.p. (MeOH) 143°-144° C. (dec.);

$[\alpha]_D$=+237° (c=1, $CHCl_3$);

U.V. (95% EtOH): $\lambda_{max}$=284 nm, $\epsilon$=10,495.

EXAMPLE 7

4-azidoandrosta-1,4,6-trien-3,17-dione [I, R=$N_3$, $R_1$=$R_2$=H, (x)=(y)=double bond]

To a stirred solution of 0.5 g of 6β-bromo-7α-acetoxyandrosta-1,4-dien-3,17-dione in 30 ml of dimethylformamide and 1.2 ml of water are added 0.11 g of sodium azide. The reaction mixture is heated at 100° C. for 45 minutes, cooled, poured into 500 ml of iced water and extracted with ethyl acetate. The combined extracts are washed with water, dried over sodium sulphate, filtered and evaporated in vacuo to give a residue which is purified by column chromatography on silica gel. Elution with n-hexane:ethyl acetate 70:30 yields 0.28 g of the title compound, m.p. 123°-125° C. (dec.);

$[\alpha]_D$=+155° (c=0.5, $CHCl_3$);

I.R. (Nujol): $\nu_{max}$=2120, 1740, 1650, 1630, 1605, 1575 $cm^{-1}$;

N.M.R. ($CDCl_3$, δ): 0.92 (3H, s); 1.18 (3H, s); 6.22 (1H, dd); 6.26 (1H, d); 6.66 (1H, dd); 7.29 (1H, d).

By proceeding analogously, the title compound is prepared from 6β,7α-dibromoandrosta-1,4-dien-3,17-dione.

EXAMPLE 8

4-azidoandrost-1,4-dien-3,17-dione [I, R=$N_3$, $R_1$=$R_2$=H, (x)=double bond, (y)=single bond]

The title compound is obtained from 4-methanesulfonyloxyandrosta-1,4-dien-3,17-dione and sodium azide following the same procedure as described in the example 3. Alternatively, the title compound is obtained from 4.5-epoxyandrost-1-en-3,17-dione and sodium azide following the same procedure as described in the example 4, m.p. 144°-146° C. (dec.), U.V. (95% EtOH): $\lambda_{max}$=239 nm, $\epsilon$=15,945, $\lambda_{max}$=303 nm, $\epsilon$=4,490;

I.R. (Nujol): $\nu_{max}$=2110, 1730, 1650, 1630, 1595, $cm^{-1}$;

N.M.R. ($CDCl_3$δ): 0.93 (3H, s); 1.25 (3H, s); 3.15 (1H, m); 6.27 (1H, d); 7.08 (1H, d).

EXAMPLE 9

4-aminoandrosta-4,6-dien-3,17-dione [I, R=$NH_2$, $R_1$=$R_2$=H, (x)=single bond, (y)=double bond]

A mixture of 0.125 g of 4-azidoandrost-4-en-3,17-dione in 10 ml of dimethylformamide and 0.4 ml of a 1N sodium azide aqueous solution is stirred and heated at 90°-100° C. for 30 minutes, during which time the evolution of nitrogen is observed. After cooling the reaction mixture is worked up as described in the example 1. There are obtained 0.085 g of the title compound, m.p. 147°-149° C. (dec.).

EXAMPLE 10

4-aminoandrost-4-en-3,17-dione [I, R=$NH_2$, $R_1$=$R_2$=H, (x)=(y)=single bond]

To a suspension of 3.83 g of 4-azidoandrost-4-en-3,17-dione in 600 ml of freshly distilled dry methanol are added 9 ml of propane-1,3-dithiol and 12 ml of triethylamine. The resulting yellow mixture is stirred at room temperature under nitrogen atmosphere for 7 hours, poured into water, brought to pH 2 with a 1N HCl aqueous solution, and washed with diethyl ether. The aqueous phase is brought to neutrality with a 2N NaOH aqueous solution and the resulting precipitate is filtered off, dried and crystallized from ethyl acetate.

There are obtained 2.60 g of the title compound, m.p. 186°-188° C.;

$[\alpha]_D$=+167° (c=1, $CHCl_3$);

U.V. (95% EtOH): $\lambda_{max}$294 nm, $\epsilon$=7,354;

N.M.R. ($CDCl_3$, δ): 0.93 (3H, s); 1.20 (3H, s); 2.90 (2H, m);

By proceeding analogously the following compounds are prepared:

4-aminoandrost-1,4-dien-3,17-dione;
4-aminoandrost-1,4,6-trien-3,17-dione

EXAMPLE 11

4-acetylaminoandrost-4,6-dien-3,17-dione [I, R=$NHCOCH_3$, $R_1$=$R_2$=H, (x)=single bond, (y)=double bond]

To a stirred solution of 2.7 g of 4-aminoandrosta-4,6-dien-3,17-dione in 10.8 ml of dry pyridine are added 5.4 ml of acetic anhydride at room temperature dropwise. After 90 minutes of additional stirring, the reaction mixture is cooled to 0° C. and worked up by the addition of cold water, followed by extraction with ethyl acetate. The organic phase is separated, washed with saturated NaCl aqueous solution, dried over $Na_2SO_4$ and evaporated in vacuo to yield a residue which is purified by column chromatography on silica gel. Elution with ethyl acetate:methanol 9:1 yields 2.6 g of the title compound as yellow crystals, m.p. 235°-236° C. (dec.);

$[\alpha]_D$=+28.4° (c=1, $CHCl_3$);

U.V. (95% EtOH): $\lambda_{max}$=293 nm, $\epsilon$=19,503;

N.M.R. ($CDCl_3$, δ): 2.12 (3H, s).

By proceeding analogously, the following compounds are prepared:

4-acetylamino-6-methylandrosta-4,6-dien-3,17-dione;
4-acetylamino-7-methylandrosta-4,6-dien-3,17-dione;
4-acetylamino-7-ethynylandrosta-4,6-dien-3,17-dione;
4-acetylamino-7-(2-propynyl)androsta-4,6-dien-3,17-dione;
4-acetylamino-7-ethylandrosta-4,6-dien-3,17-dione;

4-acetylamino-7-(1-propynyl)androsta-4,6-dien-3,17-dione;
4-acetylamino-7-vinylandrosta-4,6-dien-3,17-dione;
4-acetylamino-7-(1-butynyl)androsta-4,6-dien-3,17-dione;
4-acetylamino-7-(2-butynyl)androsta-4,6-dien-3,17-dione;
4-acetylamino-7-(3-butynyl)androsta-4,6-dien-3,17-dione.

In analogous fashion, using the anhydrides or halides, in particular chlorides, of the propionic, benzoic, hexanoic, octanoic, decanioc, dodecanoic, hexadecanoic, octadecanoic, trimethylacetic, tetradecanoic, succinic, oxalic, methanesulfonic and p-toluenesulfonic acid, the corresponding 4-carbonylamino or 4-sulfonylamino derivatives are prepared.

EXAMPLE 12

4-ethoxycarbonylaminoandrosta-4,6-dien-3,17-dione [I, R=—$NHCOOC_2H_5$, $R_1$=$R_2$=H, (x)=single bond, (y)=double bond]

To a stirred solution of 3.0 g of 4-aminoandrosta-4,6-dien-3,17-dione in 15 ml of dry pyridine, cooled to 0° to −5° C., 1.25 ml of ethylchlorocarbonate are added dropwise. The mixture is cooled and stirred for 30 minutes and then, after the temperature is left to rise to 20° C., it is quenched in 100 ml of water. The mixture is extracted several times with ethyl acetate, washed with aqueous sodium chloride solution until neutral and dried. The solvent is then distilled in vacuo to obtaind 3.2 g of crude which is purified by crystallization with warm ethyl acetate to yield 2.95 g of pure title compound, U.V. (95% EtOH): $\lambda_{max}$=294 nm, $\epsilon$=20,100.

By proceeding analogously, the following compounds are prepared:

4-benzyloxycarbonylaminoandrosta-4,6-dien-3,17-dione;
4-ethoxycarbonylaminoandrosta-1,4-dien-3,17-dione;
4-benzyloxycarbonylaminoandrosta-1,4-dien-3,17-dione;
4-ethoxycarbonylaminoandrosta-1,4,6-trien-3,17-dione;
4-benzyloxycarbonylaminoandrosta-1,4,6-trien-3,17-dione;
4-ethoxycarbonylaminoandrost-4-en-3,17-dione;
4-benzyloxycarbonylaminoandrost-4-en-3,17-dione.

EXAMPLE 13

4-aminoandrost-4-en-3,17-dione [I, R=$NH_2$, $R_1$=$R_2$=H, (x)=(y)=single bond]

To a stirred solution of 0.45 g of 4-aminoandrost-4,6-dien-3,17-dione in 20 ml of diethyl ether and 40 ml of liquid ammonia are added 0.28 g of lithium metal at small portions. The resulting blue reaction mixture is stirred for additional 30 minutes, quenched with absolute ethanol till the blue colour fades and allowed to reach the room temperature. The resulting residue is taken up with water, extracted with diethyl ether and purified as described in example 10. There are obtained 0.280 g of the title compound, m.p. 185°-187° C.

EXAMPLE 14

4-acetylaminoandrosta-1,4,6-trien-3,17-dione [I, R=—$NHCOCH_3$, $R_1$=$R_2$=H, (x)=(y)=double bond]

A solution of 0.600 g of 4-acetylamino-androsta-4,6-dien-3,17-dione in 20 ml of dry benzene is treated with 0.600 g of 2,3-dichloro-5,6-dicyano-1,4-benzoquinone (DDQ) and heated at reflux temperature. The reaction mixture is allowed to stand at 80° C. for 20 hours then is cooled to room temperature, filtered and the solid washed with ethyl acetate. The collected organic phases are washed with 5% $NaHCO_3$ aqueous solution, NaCl saturated aqueous solution, and then the solvent is removed at reduced pressure. The crude product is purified by chromatography on silica gel using ethyl acetate:methanol 95:5, to obtain 0.380 g of pure title compound;

N.M.R. ($CDCl_3$ $\delta$): 0.92 (3H, s); 1.32 (3H, s); 2.15 (3H, s); 6.12-6.50 (2H, dd); 6.35 (1H, d); 7.15 (1H, d); 7.35 (1H, br);

By proceeding analogously, the following compounds are prepared:

4-amino-6-methylandrosta-1,4,6-trien-3,17-dione;
4-amino-7-methylandrosta-1,4,6-trien-3,17-dione.

EXAMPLE 15

4-aminoandrosta-4,6-dien-3,17-dione hydrochloride [I, R=$NH_2$, $R_1$=$R_2$=H, (x)=(y)=single bond, as hydrochloride]

A solution of 0.5 g of 4-aminoandrosta-4,6-dien-3,17-dione in 20 ml of ethanol is treated with 16.7 ml of 0.1N HCl aqueous solution. The yellow solution is then treated with 0.02 g of carbon, filtered and the alcohol is distilled at reduced pressure. The resulting aqueous solution is lyophilized to give 0.54 g of dry title compound as slight yellow powder.

By analogous procedure starting from the other 4-amino compounds mentioned in examples 1, 13 and 14, the corresponding hydrochlorides are prepared and, similarly, the salts with sulfuric, phosphoric, citric, fumaric, ascorbic, malic, tartaric, benzoic, phenylacetic, cyclohexylacetic, 3-cyclohexylpropionic, methanesulfonic, benzenesulfonic, p-toluenesulfonic and p-nitrobenzenesulfonic acid are prepared for all the 4-amino compounds mentioned in examples 1, 13 and 14.

EXAMPLE 16

Tablets each weighing 0.150 g and containing 25 mg of the active substances, are manufactured as follows:

| Composition (for 10,000 tablets) | |
|---|---|
| 4-aminoandrosta-4,6-dien-3,17-dione | 250 g |
| Lactose | 800 g |
| Corn starch | 415 g |
| Talc powder | 30 g |
| Magnesium stearate | 5 g |

The 4-aminoandrosta-4,6-dien-3,17-dione, the lactose and half the corn starch are mixed; the mixture is then forced through a sieve of 0.5 mm mesh size. Corn starch (10 g) is suspended in warm water (90 ml) and the resulting paste is used to granulate the powder. The granulate is dried, comminuted on a sieve of 1.4 mm mesh size, then the remaining quantity of starch, talc and magnesium stearate is added, carefully mixed and processed into tablets.

EXAMPLE 17

Capsules, each dosed at 0.200 g and containing 20 mg of the active substance are prepared.

| Composition for 500 capsules: | |
|---|---|
| 4-acetylaminoandrosta-4,6-dien-3,17-dione | 10 g |
| Lactose | 80 g |
| Corn starch | 5 g |
| Magnesium stearate | 5 g |

This formulation is encapsulated in two-piece hard gelatin capsules and dosed at 0.200 g for each capsule.

EXAMPLE 18

Intramuscular injection 25 mg/ml

An injectable pharmaceutical composition is manufactured by dissolving 25 g of 4-aminoandrosta-4,6-dien-3,17-dione in sterile propyleneglycol (1000 ml) and ampoules of 1-5 ml are sealed.

We claim:

1. A compound of formula (I)

(I)

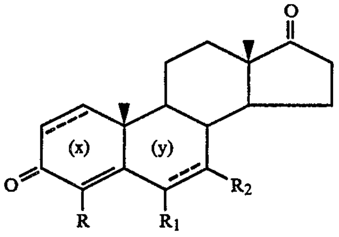

wherein

R is $NH_2$;

one of $R_1$ and $R_2$ is hydrogen and the other is hydrogen, $C_1$-$C_6$ alkyl, $C_2$-$C_6$ alkenyl or $C_2$-$C_6$ alkynyl;

and the symbol ------ indicates that each of (x) and (y), independently, is a single bond or a double bond, and the pharmaceutically acceptable salts thereof.

2. A process for the preparation of a compound of formula (I) according to claim 1, or a pharmaceutically acceptable salt thereof, the process comprising:

(A) reacting a compound of formula (II) or (IIa)

(II)

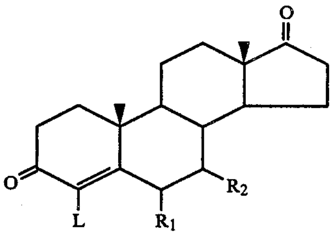

(IIa)

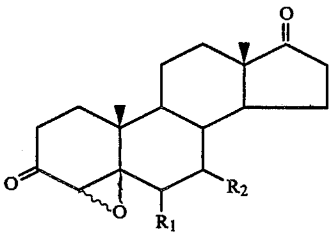

wherein $R_1$ and $R_2$ are as defined in claim 1, and L is a leaving group displaceable by nucleophilic substitution, with a compound of formula (III)

$M—N_3$ (III)

wherein M is an alkali metal or ammonium cation, or a tri-$C_1$-$C_6$-alkylsilyl group, to obtain a compound of formula (I) wherein R is $NH_2$, (x) is single bond and (y) is double bond; or (B) reacting a compound of formula (IV)

(IV)

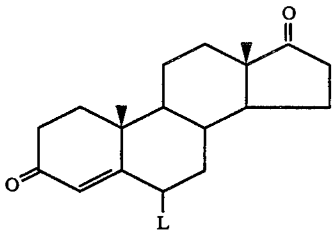

wherein L has the meaning reported above, with a compound of formula (III), to obtain a compound of formula (I) wherein R is $NH_2$, (x) is a single bond, (y) is double bond, and $R_1$ and $R_2$ are both hydrogen; or (C) pyrolysing a compound of formula (I) wherein R is the group $—N_3$ and (x) and (y) are both single bonds, to obtain a compound of formula (I) wherein R is $NH_2$, (x) is single bond and (y) is double bond; or (D) reducing a compound of formula (I) wherein R is the group $—N_3$, to obtain a compound of formula (I) wherein R is $NH_2$ and/or, if desired, reducing a compound of formula (I) wherein (x) is single bond and (y) is double bond to obtain a corresponding compound of formula (I) wherein (x) and (y) are both single bonds and/or, if desired, oxidizing a compound of formula (I) wherein (x) is single bond, to obtain a corresponding compound of formula (I) wherein (x) is double bond and/or, if desired, converting a compound of formula (I) into another compound of formula (I) and/or, if desired, salifying a compound of formula (I) or obtaining a free compound of formula (I) from a salt thereof and/or, if desired, separating a mixture of isomers of formula (I) into the single isomers.

3. A pharmaceutical composition comprising a pharmaceutically acceptable carrrier and/or diluent and, as the active substance, a compound of formula (I) or a pharmaceutically acceptable salt thereof, according to claim 1.

4. A method of producing aromatase inhibition in a patient in need of it, the said method comprising administering an effective amount of a composition according to claim 3.

5. A method of producing aromatase inhibition in a patient in need of it, the said method comprising administering an effective amount of a compound according to claim 1.

6. A compound selected from the group consisting of:
4-aminoandrost-4-en-3,17-dione;
4-aminoandrosta-4,6-dien-3,17-dione;
4-amino-6-methylandrosta-4,6-dien-3,17-dione;
4-amino-7-methylandrosta-4,6-dien-3,17-dione;
4-aminoandrosta-1,4,6-trien-3,17-dione;
4-amino-6-methylandrosta-1,4,6-trien-3,17-dione;
4-amino-7-methylandrosta-1,4,6-trien-3,17-dione;
4-amino-7-ethynylandrosta-4,6-dien-3,17-dione;
4-amino-7-(2-propynyl)androstsa-4,6-dien-3,17-dione;
and the pharmaceutically acceptable salts thereof.

* * * * *